US 6,589,053 B2

(12) United States Patent
Bills (10) Patent No.: US 6,589,053 B2
(45) Date of Patent: Jul. 8, 2003

(54) LOW PROFILE MATRIX BAND RETAINERS (75) Inventor: Dan J. Bills, Salt Lake City, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/074,848

(22) Filed: Feb. 13, 2002

(65) Prior Publication Data
US 2003/0059741 A1 Mar. 27, 2003

Related U.S. Application Data (63) Continuation-in-part of application No. 09/838,681, filed on Apr. 19, 2001, now abandoned.

(51) Int. Cl.[7] .................................................. A61C 5/12
(52) U.S. Cl. ........................ 433/139; 433/149; 433/153
(58) Field of Search .......................... 433/39, 139, 153, 433/149

(56) References Cited

U.S. PATENT DOCUMENTS

| 164,870 A |   | 6/1875 | Palmer ........................ 433/139 |
| 427,338 A | * | 5/1890 | Marshall ....................... 433/39 |
| 1,031,533 A |   | 7/1912 | Davidson ..................... 433/139 |
| 1,336,746 A |   | 4/1920 | Ivory .......................... 433/139 |
| 2,507,938 A |   | 5/1950 | Smith .......................... 433/139 |
| 2,706,333 A |   | 4/1955 | Schultz ........................ 433/139 |
| 4,004,345 A |   | 1/1977 | Ely ............................. 433/139 |
| 4,265,623 A |   | 5/1981 | Soelberg et al. ............. 433/139 |
| 4,373,915 A |   | 2/1983 | Comstock ................... 433/136 |
| 4,601,662 A |   | 7/1986 | Galler ........................ 433/226 |
| 4,639,221 A |   | 1/1987 | Sairenji ...................... 433/139 |
| 4,661,063 A |   | 4/1987 | Levy .......................... 433/139 |
| 4,718,852 A |   | 1/1988 | Galler ........................ 433/148 |
| 4,787,849 A |   | 11/1988 | Jacoby et al. ............... 433/139 |
| 5,199,869 A |   | 4/1993 | McGann ...................... 433/21 |
| 5,314,331 A |   | 5/1994 | Brosius et al. ............... 433/21 |
| 5,503,556 A |   | 4/1996 | Leonard et al. ............ 433/139 |
| 5,607,302 A |   | 3/1997 | Garrison et al. ............. 433/39 |
| 5,975,906 A |   | 11/1999 | Knutson ..................... 433/226 |
| 5,993,210 A |   | 11/1999 | Godfrey ..................... 433/159 |
| 6,206,697 B1 | * | 3/2001 | Hugo .......................... 433/39 |
| 6,293,796 B1 | * | 9/2001 | Trom et al. ................. 433/139 |
| 6,325,625 B1 |   | 12/2001 | Meyer ........................ 433/139 |

* cited by examiner

Primary Examiner—John J. Wilson
(74) Attorney, Agent, or Firm—Workman, Nydegger & Seeley (57) ABSTRACT The invention comprises improved matrix band retainers for use in dental procedures. The matrix band retainers comprise a pair of tines anatomically configured to be inserted into the interproximal spaces between adjacent teeth for holding a matrix band in proper alignment during a dental filling procedure. The matrix band retainers have a thin profile characterized by the cross-sectional area of the flexible body member in which the width of the body is greater than the height of the body. The tines are connected to the flexible body member by crossbar members. The matrix band retainers also comprise receptacle means for securely receiving the prongs of a spreading device. The receptacle means may include hole formations formed in the body member configured for engaging the prongs of a rubber dam clamp spreading tool.

20 Claims, 6 Drawing Sheets

FIG. 9

LOW PROFILE MATRIX BAND RETAINERS

CROSS-REFERENCE TO RELATED APPLICATION

This application is a continuation-in-part of U.S. patent application Ser. No. 09/838,681, entitled, ANATOMICALLY SHAPED SECTIONAL MATRIX BAND RETAINERS, filed Apr. 19, 2001, now abandoned, which is incorporated herein by reference.

BACKGROUND OF THE INVENTION

1. The Field of the Invention

The present invention is in the field of matrix band retainers for use in dental procedures. In particular, the present invention relates to matrix band retainers configured to be inserted into the interproximal spaces between teeth for holding a matrix band in proper placement during dental filling procedures.

2. The Prior State of the Art

In the field of dentistry, dental practitioners often treat patients who have developed cavities in a tooth. In order to treat cavities the dental practitioner removes the infected portion of the tooth and then deposits a filling material such as a composite, a resinous material, or an amalgam into the tooth preparation.

During the dental filling procedure, a matrix band is typically placed against the side of the tooth to approximately define the desired shape of the restored tooth and to keep the filling material from flowing beyond the desired tooth boundary. A matrix band typically comprises a thin metallic or plastic strip that is flexible and can be bent around the tooth being restored. The matrix band is particularly useful because it provides form for the desired shape of the resultant filling. However, if the matrix band is not properly held in place then too much or too little filling material may be deposited into the tooth preparation, thereby distorting the configuration of the restored tooth.

An improper filling can lead to dental discomfort, misaligned teeth, capture of food particles, infections, and other dental problems. To avoid these problems and to fix a distorted dental filling, it may be necessary to grind or drill the filling material down to the proper shape. It is desirable, however, to avoid this process because it increases the time and cost of performing the filling procedure and can create anxiety and discomfort for the patient.

In order to place the matrix band into a desired placement, it is sometimes necessary to separate the teeth by placing small dental wedges in the interproximal spaces between the teeth. One inherent problem with the use of matrix bands and dental wedges, however, is that they are susceptible to moving and slipping out from between the teeth. In an attempt to avoid this problem, dental practitioners have used clamps, commonly known as matrix band retainers, to hold the matrix band and dental wedges in place during the filling procedure.

Conventional matrix band retainers consist of a rigid, cylindrical wire bent so as to have a generally circular body and one of two generally straight tines extending perpendicularly from each end of the circular body. During use, the tines are spread open and placed in the interproximal spaces between the tooth being repaired and an adjacent tooth. One problem with such matrix band retainers is that the tines do not anatomically conform to the shape of the teeth. This results in inadequate retention of the matrix band such that the matrix band in an anatomically correct conformation. In addition, such matrix bands can easily slip out of position.

Another problem concerns the initial placement of the conventional matrix band retainer. The flexible frame or body of conventional matrix band retainers is typically a rigid, cylindrical wire that has been bent to have a generally circular configuration. The rigidity of the wire helps create a strong, spring-like action. It also, however, makes it difficult to spread the tines apart by hand.

To provide additional leverage to spread the tines apart, conventional rubber dam clamp spreading tools may be used to spread the tines apart. However, existing matrix band retainers are not specifically configured to receive the prongs of the rubber dam clamp spreading tool. Accordingly, the use of a rubber dam clamp spreading tool to spread the tines can be unsafe. For example, it has been found that the matrix band retainer can slip off the prongs of the rubber dam clamp spreading tool, making the procedure both difficult and unsafe.

Yet another problem with conventional matrix band retainers is that it is often difficult for them to overlap while enabling the tines of the overlapping retainers to be appropriately positioned during a dental procedure. In particular, the profile, or cross-sectional height, of conventional matrix band retainers is typically the same as the width, which can cause the overlapping matrix band retainer to be angularly displaced by the height of the underlying matrix band retainer. This angular displacement can cause the corresponding tines of the overlapping matrix band retainer to engage the dental surfaces in an irregular fashion. This can be problematic when the tines are used to provide a biasing support for holding a matrix band against a tooth receiving a dental restoration. Irregular alignment of the tines with the matrix band can cause correspondingly bad alignment of the matrix band, thereby resulting in the formation of an irregular dental restoration. It may also result in unwanted slippage of the matrix band, matrix band retainer, or both.

Accordingly, there is currently a need in the art for improved matrix band retainers. In particular, there is a need for matrix band retainers that are configured to better conform to the dental surfaces of teeth so as to better hold matrix bands in desired and proper placement during dental procedures. It would also be desirable to provide such improved matrix band retainers that are configured for overlapping another matrix band retainers during use. It would also be desirable to provide improved matrix band retainers that are specifically configured to more securely and reliably receive the prongs of a conventional rubber dam clamp spreading tool or other spreading tool. Such improved matrix band retainers are disclosed and claimed herein.

SUMMARY OF THE INVENTION

The present invention is directed to improved matrix band retainers for use in dental filling procedures. The matrix band retainers of the invention comprise tines that are anatomically configured in size and shape to better fit within the interproximal spaces between adjacent teeth for providing increased contact with the surfaces against which the matrix band retainer is placed. Such matrix band retainers are able to retain a matrix band in an anatomically correct configuration during a dental filling procedure without separating the adjacent teeth. The matrix band retainers of the invention are also specifically configured to more securely receive the prongs of a rubber dam clamp spreading tool for spreading the tines of the matrix band retainer in a safe and secure manner.

In one preferred embodiment of the invention, the matrix band retainer comprises two tines, a flexible body member, two crossbar members separating the tines from the body member, and receptacle means for securely receiving the prongs of a separating device.

An example of receptacle means includes a pair of hole formations extending through the body member. For instance, during use, the prongs of a rubber dam clamp spreading tool are inserted within the hole formations and a spreading force is applied with the rubber dam clamp, thereby causing the flexible body member to flex outwardly and the tines to spread apart. Once the tines are sufficiently spread apart they are placed into the interproximal spaces between the matrix band and adjacent tooth. Once the rubber dam clamp spreading tool is removed, the spring-back force of the body member urges the tines against the matrix band and adjacent tooth with a holding force that is sufficient for holding the matrix band in a desired placement without separating the adjacent teeth.

According to the invention, each of the tines is interconnected with the body member by a different one of the crossbar members. According to one embodiment, the crossbar members are generally concentric and lay in planar alignment with the body member. The crossbar members advantageously enable the matrix band retainer to be configured with a wide body member for enabling access to the dental surfaces around which the matrix band retainer is placed. The crossbar members also enable the tines to be positioned sufficiently close together, regardless of the width of the body member. Yet another benefit of the crossbar members is that they advantageously position the aforementioned receptacle means at the ends of the main body member such that the receptacle means are spaced-apart from the tines by the length of the cross bar members. This may be useful in reducing the force required to separate the tines with the rubber dam clamp spreading tool, while at the same time spacing the receptacle means away from the tines for reducing any risk that the prongs of the separating device will abrade or otherwise damage dental surfaces disposed proximate the tines, such as during placement and removal of the matrix band retainer.

According to one embodiment, the tines are curved so as to approximate the curvature of teeth, typically molars or bicuspids. In this manner, each tine provides an anatomical bearing surface for urging the matrix band to better conform to the shape of the tooth being restored, particularly, the outer curved surface of the tooth.

In the same or alternative embodiments, the tines may be approximately wedge-shaped so that an acutely angled edge portion of each tine can be inserted more deeply into the corresponding interproximal space between the tooth being filled and an adjacent tooth for providing an anatomical bearing surface that more closely approximates the dental surfaces of the adjacent teeth. Alternatively, the tines may be square, rectangular, ellipsoidal or circular in cross section.

The body member, the crossbar members, the tines and the retention means are all preferably manufactured out of a single piece of material, such as stainless spring steel, thereby minimizing any costs associated with manufacturing and connecting the different components of the matrix band retainer. It will be appreciated, however, that the body member, the tines, and the crossbar members may also be manufactured separately and out of different materials, such as plastic. Preferably, at least the body member is composed of a resilient and flexible material for enabling the body member to resiliently bend when the tines are separated by a rubber dam clamp spreading tool, as generally described above, for enabling the body member to urge the tines together with sufficient force for holding a matrix band in a desired placement against a tooth once the rubber dam clamp spreading tool is removed.

According to the preferred embodiment of the invention, and under normal conditions, the force provided by the body member is sufficient for holding the tines in a desired placement, yet insufficient for substantially separating the teeth between which the tines are placed. In particular, the tines will preferably not provide so much of a spreading force that two initially abutting teeth of normal tightness will spread apart sufficiently so that a matrix band can be placed between the teeth absent the application of an additional tooth spreading force, e.g., by means of dental wedges.

According to other embodiments of the invention, the matrix band retainer is configured to overlap at least one other retainer during use. To minimize angular displacement between overlapping matrix band retainers of the invention, the body member and the crossbar members are configured with a thin profile. Excessive angular displacement caused by existing matrix band retainers may cause the corresponding tines to bias against the teeth in a manner that does not anatomically correspond with the shape of the teeth, thereby reducing the ability of the matrix band retainers to hold a matrix band in an appropriate placement against a tooth for providing a desired form. According to this embodiment, the cross-sectional width of the body member and the crossbar members is substantially greater than the corresponding cross-sectional height (or thickness), thereby enabling the matrix band retainer to provide an adequate holding force for holding a matrix band in a desired placement, despite the thin profile of the matrix band retainer.

One benefit of the invention is that it generally enables a plurality of matrix band retainers to overlap during use without causing the tines of the overlapping matrix band retainers to be angularly offset from their desired placements within or proximate the interproximal spaces between the teeth. Another benefit of the matrix band retainer of the invention is that it provides retention means for enabling the tines of the matrix band retainer to be spread apart with a rubber dam clamp spreading tool in a safe and secure manner. The invention also generally provides tines that are anatomically configured to be more easily inserted into the interproximal spaces between teeth for providing increased contact between a matrix band and the tooth being filled so as to urge the matrix band into a more anatomically correct configuration, while reducing the likelihood that the matrix band retainer will slip out of its holding position.

These and other features and advantages of the present invention will become more fully apparent from the following description and appended claims, or may be learned by practicing the invention as set forth below.

BRIEF DESCRIPTION OF THE DRAWINGS

A more extensive description of the present invention, including the above-recited features and advantages, will be rendered with reference to the specific embodiments that are illustrated in the appended drawings. Because these drawings depict only exemplary embodiments, the drawings should not be construed as imposing any limitation on the present invention's scope. As such, the present invention will be described and explained with additional specificity and detail through use of the accompanying drawings in which.

DETAILED DESCRIPTION OF THE PREFERRED EMBODIMENTS

The present invention relates to improved matrix band retainers for use in dental filling procedures. More particularly, the present invention relates to thin profile matrix band retainers configured in size and shape for reducing any angular displacement of the corresponding tines during use in which the matrix band retainers overlap. The matrix band retainers of the invention are also configured to receive the prongs of a rubber dam clamp spreading tool for spreading the tines apart in a safe and secure manner.

Certain terms used in this application will now be defined to provide context for interpreting the scope of the claimed invention.

The term "holding force" as used herein, applies to the resilient spring force exerted by the matrix band retainer when the tines of the matrix band retainer have been forcibly separated. The "holding force," according to the invention, is adequate for pressing and holding a matrix band against the surface of a tooth, but is preferably insufficient for independently causing two abutting teeth of normal tightness to separate sufficiently so as to receive a matrix band therebetween absent the application of an independent tooth-spreading force (e.g., by one or more dental wedges).

The term "hole formation," as used herein, refers to the surfaces, walls, and other structural features defining the boundaries of an aperture, a hole, a perforation, an indentation, a recess, a groove, or other void. Inasmuch as the term "hole formation" is specifically associated, herein, with receptacle means for securely receiving the prongs of a separating device, such as a rubber dam clamp spreading tool, that can be used to separate the tines of the matrix band retainer, "the hole formation" is at least sized or shaped for securely receiving and engaging the prong of a rubber dam clamp spreading tool. In a preferred embodiment, as described herein, the hole formation is configured to support the prong of a rubber dam clamp spreading tool from at least two opposite directions.

The terms "height" and "thickness" are used interchangeably in the specification and claims, and refer to the same dimension, unless otherwise noted.

Figure 1A:
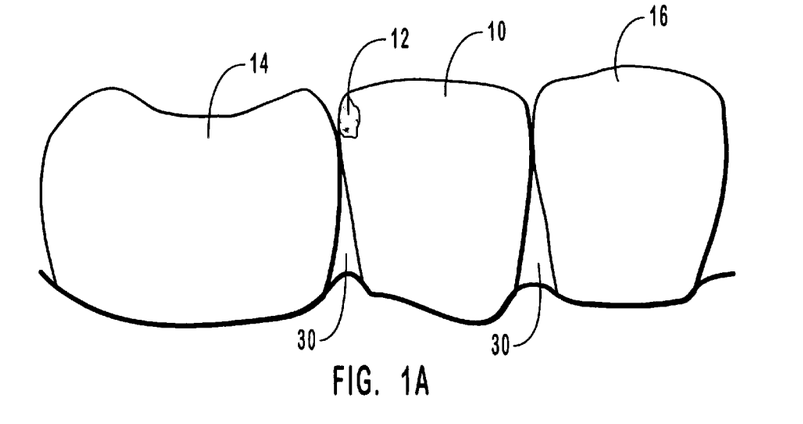
FIG. 1A is a side view of a tooth having a cavity and two adjacent teeth.
Figure 1B:
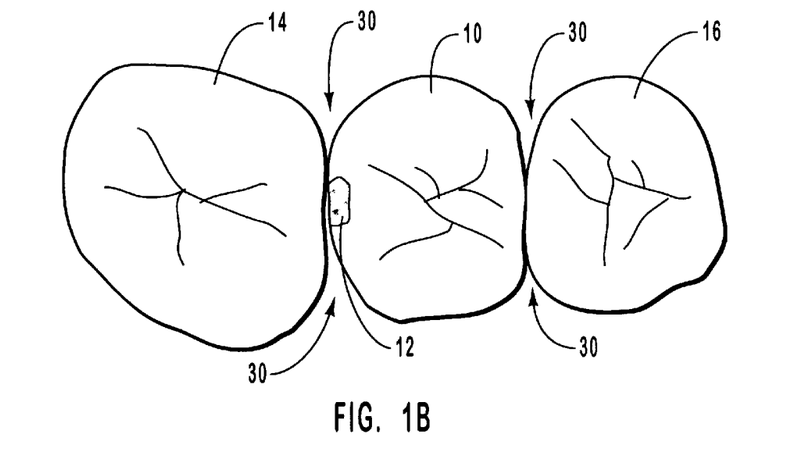
FIG. 1B is a top view of the tooth of FIG. 1A and two adjacent teeth.
Figure 1C:
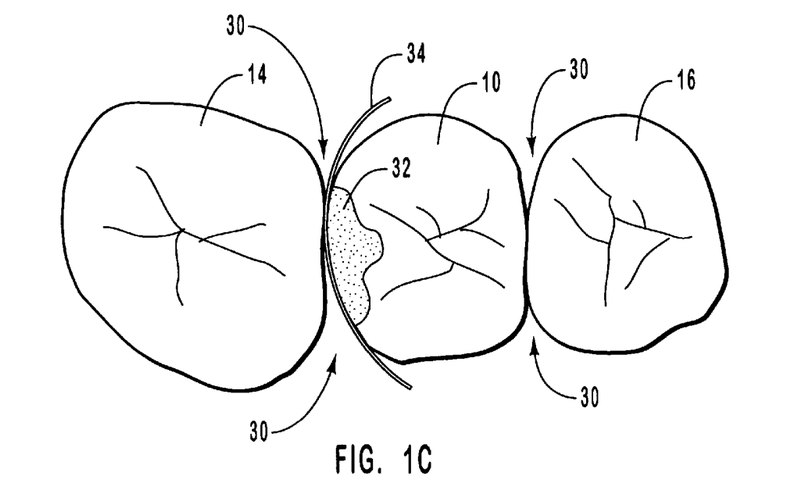
FIG. 1C is a top view of the tooth of FIG. 1A with a hollowed out dental preparation existing in the general area of the cavity of FIG. 1B and a matrix band placed between the tooth having the dental preparation and an adjacent tooth.

In the interest of clarity and to further define the terms that are used in the present application, introductory FIGS. 1A–1C are provided. FIG. 1A shows a side view of a tooth 10 having a cavity 12 and adjacent teeth 14 and 16. As shown, interproximal spaces 30 exist between tooth 10 and each of the adjacent teeth 14 and 16. The term "interproximal space," as used herein, should be generally construed to include any space between two adjacent teeth, including spaces existing proximate the gingiva, lingual surfaces, buccal surfaces, labial surfaces, and any other space existing between two adjacent teeth.

FIG. 1B shows a top view of the teeth of FIG. 1A and further illustrates the location of the interproximal spaces 30 existing between tooth 10 and each of the adjacent teeth 14 and 16.

FIG. 1C illustrates a dental preparation 32 formed within tooth 10. Dental preparation 32 is created by removing portions of tooth 10 with a drill or another suitable device. Typically, a dental preparation is formed to remove infected and damaged portions of a tooth, such as cavity 12 of FIG. 1B. Once a dental preparation is formed, a matrix band is placed against the tooth for providing form for receiving a filling material within the dental preparation. FIG. 1C illustrates how a matrix band 34 might be placed between two adjacent teeth in preparation for receiving a dental filling. When the teeth 10 and 14 need to be separated before the matrix band 34 can be placed, conventional dental wedges (not shown) may be used to separate the teeth 10 and 14.

The matrix band retainers of the present invention may be used to retain any thin, flexible matrix band in place in a more anatomically correct fashion, including anatomical matrix bands. Anatomical matrix bands that better conform to the shape of teeth are set forth in co-pending U.S. application Ser. No. 09/838,694, filed Apr. 19, 2001, entitled "Asymmetric Sectional Matrix Bands". Matrix band clamps for use in retaining matrix bands are disclosed in co-pending U.S. application Ser. No. 09/838,681, filed Apr. 19, 2001, now abandoned entitled "Anatomically Shaped Sectional Matrix Band Retainers". For purposes of disclosure, the foregoing applications are incorporated herein by reference.

Although dental filling procedures requiring the use of matrix band retainers are generally limited to the restoration of bicuspids and molars, it should be appreciated that the present invention is not limited to any particular dental procedure nor to the application of a dental procedure to any particular type of tooth.

Figure 2:
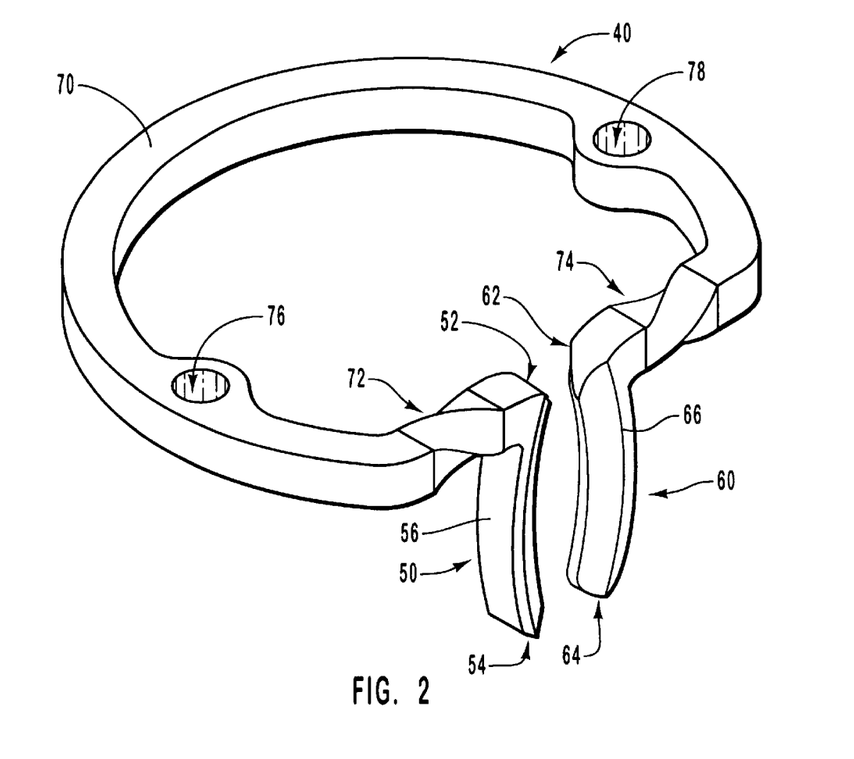
FIG. 2 is a top perspective view of one embodiment of the a matrix band retainer of the invention that includes two tines having curved and wedge-shaped bodies which are connected by a body member and two crossbar members.

Turning now to FIG. 2, one presently preferred embodiment of a matrix band retainer 40 of the invention is illustrated. As shown, a first tine 50 and a second tine 60 are connected together by a flexible and resilient arcuate body member, designated as body member 70. The first and second tines 50 and 60 comprise proximal ends 52 and 62, respectively, which are attached to body member 70, and opposing distal ends 54 and 64, respectively. The first and second tines 50 and 60 also comprise bodies 56 and 66 that extend between proximal ends 52 and 62 and distal ends 54 and 64, respectively.

In one embodiment, body member 70 and tines 50 and 60 are formed by shaping a single piece of generally rigid wire. In one presently preferred embodiment, matrix band retainer 40 comprises stainless spring steel for providing member 70 with flexibility and resiliency. It should be appreciated, however, that any appropriate material can be used to form matrix band retainer 40 and corresponding components. Suitable materials can include various metals, plastics, and flexible ceramics. In the present embodiment, body member 70 also comprises crossbar members 72 and 74. According to one embodiment, crossbar members 72 and 74 are generally concentric and lay in planar alignment with body member 70. As illustrated, the crossbar members 72 and 74 may include twisted segments, which are formed by twisting tines 50 and 60 perpendicularly to member 70 during manufacture of the matrix band retainer 40.

The crossbar members 72 and 74 advantageously enable the matrix band retainer to be configured with a wide body member 70, thereby enabling access to the dental surfaces around which the matrix band retainer 40 is placed, while at the same time enabling the tines 50 and 60 to be positioned sufficiently close together. As described below in more detail, the crossbar members 72 and 74 also advantageously separate hole formations 76 and 78 away from the tines 50 and 60. This separation between the tines 50 and 60 and the receptacle means is beneficial for at least reducing any risk that the prongs of the separating device will abrade or otherwise damage dental surfaces disposed proximate the tines, such as during placement and removal of the matrix band retainer 40. In particular, hole formations 76 and 78 comprise one suitable receptacle means for securely receiving the prongs of a separating device. During use, the prongs of a rubber dam clamp spreading tool are inserted into hole formations 76 and 78 and a spreading force is applied with the rubber dam clamp spreading tool that forces member 70 to bend outwardly, causing tines 50 and 60 to spread apart. Once tines 50 and 60 are sufficiently spread apart they can be inserted into the interproximal spaces existing between a tooth and a matrix band for holding the matrix band in proper placement for receiving a dental filling. Accordingly, it should be appreciated that by separating the hole formations 76 and 78 away from the tines 50 and 60, the crossbar members 72 and 74 are effectively able to reduce any likelihood that the prongs will abrade the dental surfaces against which the tines 50 and are placed.

In FIGS. 2, 3, and 7–9, the receptacle means are shown to comprise hole formations 76 and 78 that are rounded and specifically configured in size and shape to receive the prongs of a rubber dam clamp spreading tool. It will be appreciated, however, that the receptacle means of the invention may also comprise other shapes and configurations, including, but not limited to apertures, perforations, indentations, recesses, grooves, or other voids, and even perforations.

Figure 3:
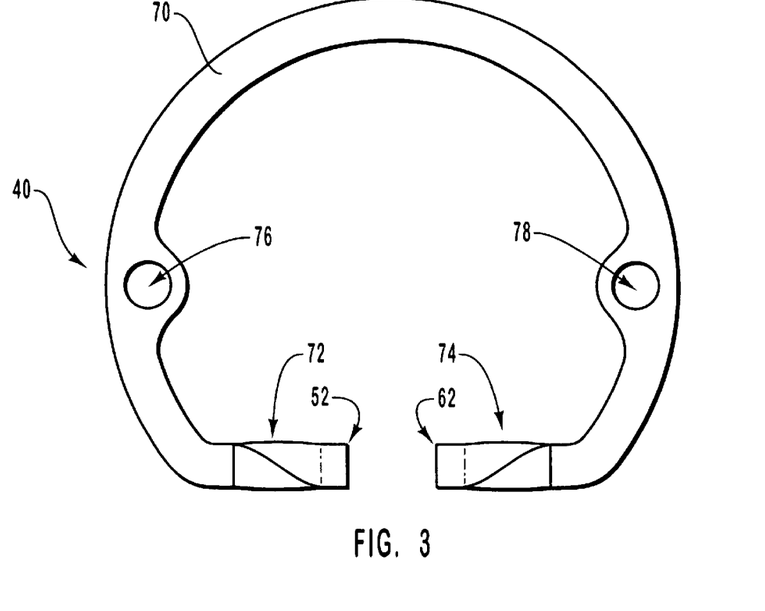
FIG. 3 is a top view of one embodiment of the matrix band retainer of the invention that includes receptacle means comprising two hole formations configured to receive the prongs of a rubber dam clamp spreading tool.

FIG. 3 is a top view of a matrix band retainer 40 according to the present embodiment. As shown, body member 70 has a generally curved shape and resembles a C-ring. This is merely illustrative, however, and should not be construed as a limitation. In particular, body member 70 can embody virtually any shape so long as it is appropriately configured for use in dental procedures and provides the desired holding force. For example, in one alternative embodiment, member 70 comprises a substantially rectilinear shape.

The desired holding force provided by the body member 70, according to the invention, is adequate for holding a matrix band in a desired placement against a tooth, but is preferably insufficient for spreading two initially abutting teeth apart so as to receive a matrix band therebetween. An auxiliary spreading device (not shown, e.g., a dental wedge) is typically required to spread apart two initially abutting teeth. Although not specifically designed as such, it will be appreciated that the matrix band retainer 40 of the invention may incidentally spread two adjacent teeth apart. In some cases, the spreading force may be enough to spread two adjacent teeth apart sufficiently so that a matrix band can be placed therebetween, e.g., when the adjacent teeth are anchored by periodontal fibers that are abnormally weak.

Figure 4:
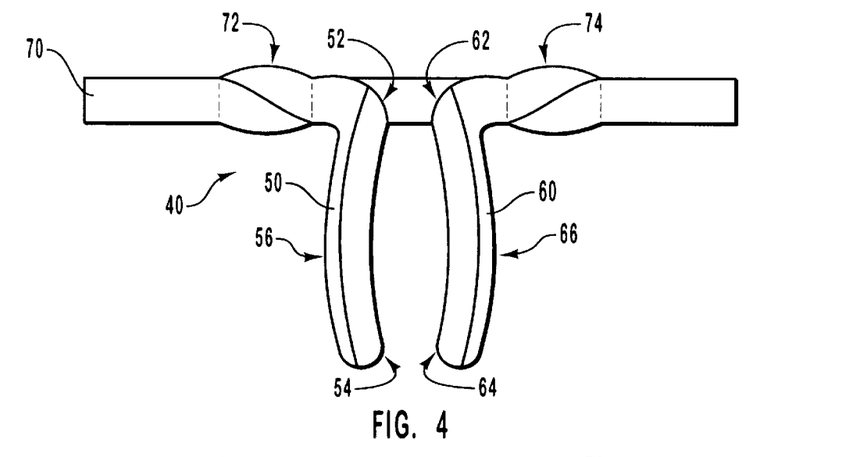
FIG. 4 is a front view of one embodiment of the matrix band retainer of the invention that includes two tines, in which each tine has a curved body.

FIG. 4 illustrates a front view of one embodiment of the matrix band retainer 40 of the invention in which tines 50 and 60 comprise curved bodies 56 and 66, respectively. The curvature of tine bodies 56 and 66 is formed by bending tines 50 and 60 during a manufacturing process. The exact radius of the curvature can be predetermined and may vary from one embodiment to another for enabling the matrix band retainer to better conform to the size and shape of different teeth. Accordingly, it will be appreciated that the radius of curvature of tine body 56 can vary from the radius of curvature of tine body 66. In one presently preferred embodiment, however, the radius of curvature for each of the tine bodies 56 and 66 is the same and is approximately ½ inch. The curvature of tine bodies 56 and 66 is such that when tines 50 and 60 are inserted in the interproximal spaces between teeth, proximal and distal ends 52, 62, 54, and 64 make contact with the surfaces against which the tines 50 and 60 are placed. It should be appreciated that curved tines 50 and 60 more closely approximate the tooth anatomy than do straight tines. Because tines 50 and 60 are curved, they are able to tightly wrap around the teeth against which they are placed, thereby holding the matrix band retainer in place and urging the matrix band into a more anatomically correct configuration against the side of the tooth being restored.

Figure 5:
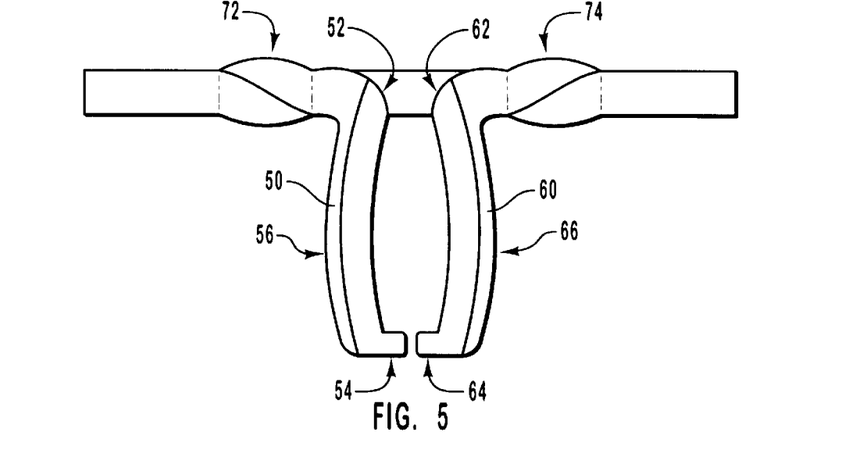
FIG. 5 is a front view of one embodiment of the matrix band retainer of the invention that comprises two tines, each having a curved body and a protruding foot that generally points towards the foot of the alternate tine.

The shape and size of the tines 50 and 60 can vary to accommodate the anatomical shape of any tooth. In some instances, the base of the exposed tooth, near the gingiva, is recessed significantly. In these instances, for example, the distal end of each tine 50 and 60 may optionally be configured with a protruding foot 54 and 64, respectively, as illustrated in FIG. 5, for providing additional contact with the tooth surface against which the tine is placed. The cross section of tines 50 and 60 can be square, rectangular, circular, or wedge-shaped as desired.

As shown in FIG. 5, distal ends 54 and 64 include feet 54B and 64B, respectively. Feet 54B and 64B extend away from their respective distal ends 54 and 64 towards the alternate distal end 54 or 64. The configuration of feet 54B and 64B and the curvature of the tine bodies 56 and 66 generally approximate the anatomical shape of the interproximal spaces between teeth, such that when tines 50 and 60 are inserted into interproximal spaces, feet 54B and 64B and bodies 56 and 66 make contact with matrix band and tooth surfaces from within the interproximal spaces between the teeth. This feature of the invention is useful because it substantially secures the matrix band retainer in the latitudinal direction, reducing the likelihood that the matrix band retainer will slip out of place, and enables the matrix band retainer to urge the matrix band into an anatomically correct configuration against the surface of the tooth that is being restored during the dental filling procedure.

Figure 6:
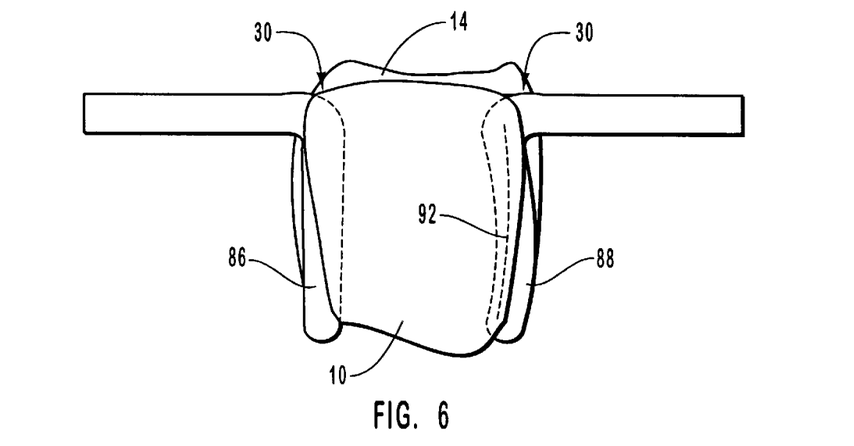
FIG. 6 is front view of two teeth and two tines positioned in the interproximal spaces between the teeth.

FIG. 6 further illustrates how the tines of the matrix band retainer 40 of the invention are anatomically configured to be inserted into the interproximal spaces between teeth. By way of comparison, a straight tine 86 and a curved tine 88 are placed in interproximal spaces 30 between tooth 10 and adjacent tooth 14. Like most bicuspids and molars, teeth 10 and 14 have profiles that are generally rounded and trapezoidal.

Curved tine 88, which is one embodiment of the tine of the matrix band retainer of the invention, is curved so as to be anatomically configured to the shape of the interproximal spaces 30 between teeth 10 and 14. As shown, curved tine 88 makes contact with the surface of tooth 10 over a region that substantially extends the entire length of curved tine 88. Contact region 92 shows the region of contact that curved tine 88 makes with tooth 10. Curved tine 88 also makes similar contact with adjacent tooth 14. When a matrix band is placed between curved tine 88 and tooth 10 then curved tine 88 urges the matrix band into an anatomically correct configuration against the surface of tooth 10 for providing form for receiving a dental filling.

Straight tine 86, which is another embodiment of the tine of the matrix band retainer of the invention, has a cross-sectional area that is anatomically configured to be inserted deeply within the interproximal spaces 30 between teeth 10 and 14. The cross-sectional shape of straight tine 86 and curved tine 88, according to one embodiment, may be generally wedge-shaped for enabling the tines 86 and 88 to be inserted more deeply and securely within the interproximal spaces between the teeth. It will be appreciated, however, that the wedge shape is not intended to forcibly wedge between and separate two adjacent teeth, although some incidental separation may occur. According to other embodiments (not shown) the contact surfaces of the tines may comprise contours that better approximate the generally round circumference of a tooth, further enabling the tines to urge and hold the matrix band in a desired placement.

It will be appreciated that although the tines have been shown in certain embodiments to comprise specific shapes, the tines of the matrix band retainer are not limited to any predefined shape. Rather, the tines can comprise any shape that is configured to conform to the anatomical shape of teeth and to be inserted into the interproximal spaces between teeth. As described above, this is accomplished by providing tines that are curved. In other embodiments, this is accomplished by providing tines that are wedge-shaped.

Certain figures of the application illustrate tines of the matrix band retainer inserted within the interproximal spaces between bicuspids and molars. Nevertheless, it will be appreciated that the invention is not limited to the practice of dental procedures on any particular type of tooth. Accordingly, the tines of the matrix band retainer of the invention can also be appropriately configured to conform to the anatomical shape of the interproximal spaces between cuspids, laterals, and centrals.

Furthermore, it should also be appreciated that references to tines of the matrix band retainer being inserted into the interproximal spaces between a matrix band and an adjacent tooth are only illustrative and not restrictive. In particular, the tines of the matrix band retainer of the invention can be placed into the interproximal spaces between two adjacent matrix bands, or between a tooth and a dental wedge, or between a dental wedge and a matrix band, or between two dental wedges, or between any combination of the foregoing.

Figure 7:
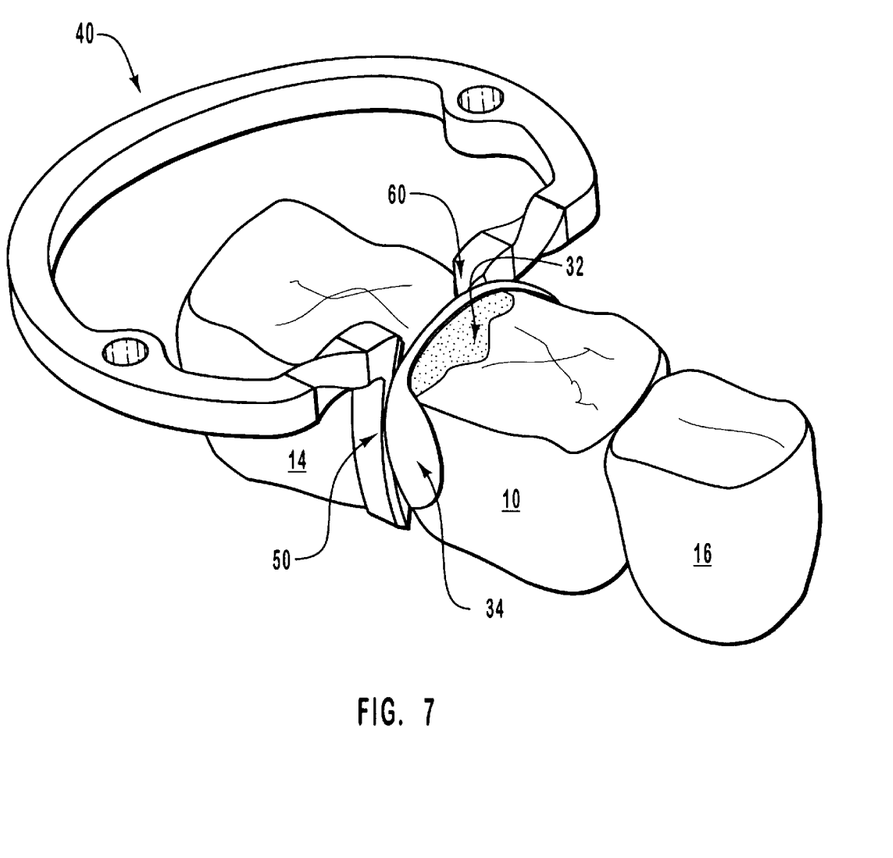
FIG. 7 is a top perspective view of the matrix band retainer of the invention positioned about two teeth with the tines of the matrix band retainer inserted within the interproximal spaces between the teeth, while holding a matrix band in place against one of the teeth that has a hollow dental preparation suitable for receiving a filling material.

For example, as shown in FIG. 7, matrix band retainer 40 can also be used to hold a matrix band 34 in a desired placement against a tooth 10 for providing form for filling a hollow dental preparation 32 with a filling material. According to the present embodiment, tines 50 and 60 of matrix band retainer 40 are both curved and somewhat wedge-shaped. As shown, tines 50 and 60 are inserted within the interproximal spaces between teeth 10 and 14. From this position, tines 50 and 60 apply a direct contact force to matrix band 170, thereby holding matrix band 34 in a desired placement.

Figure 8:
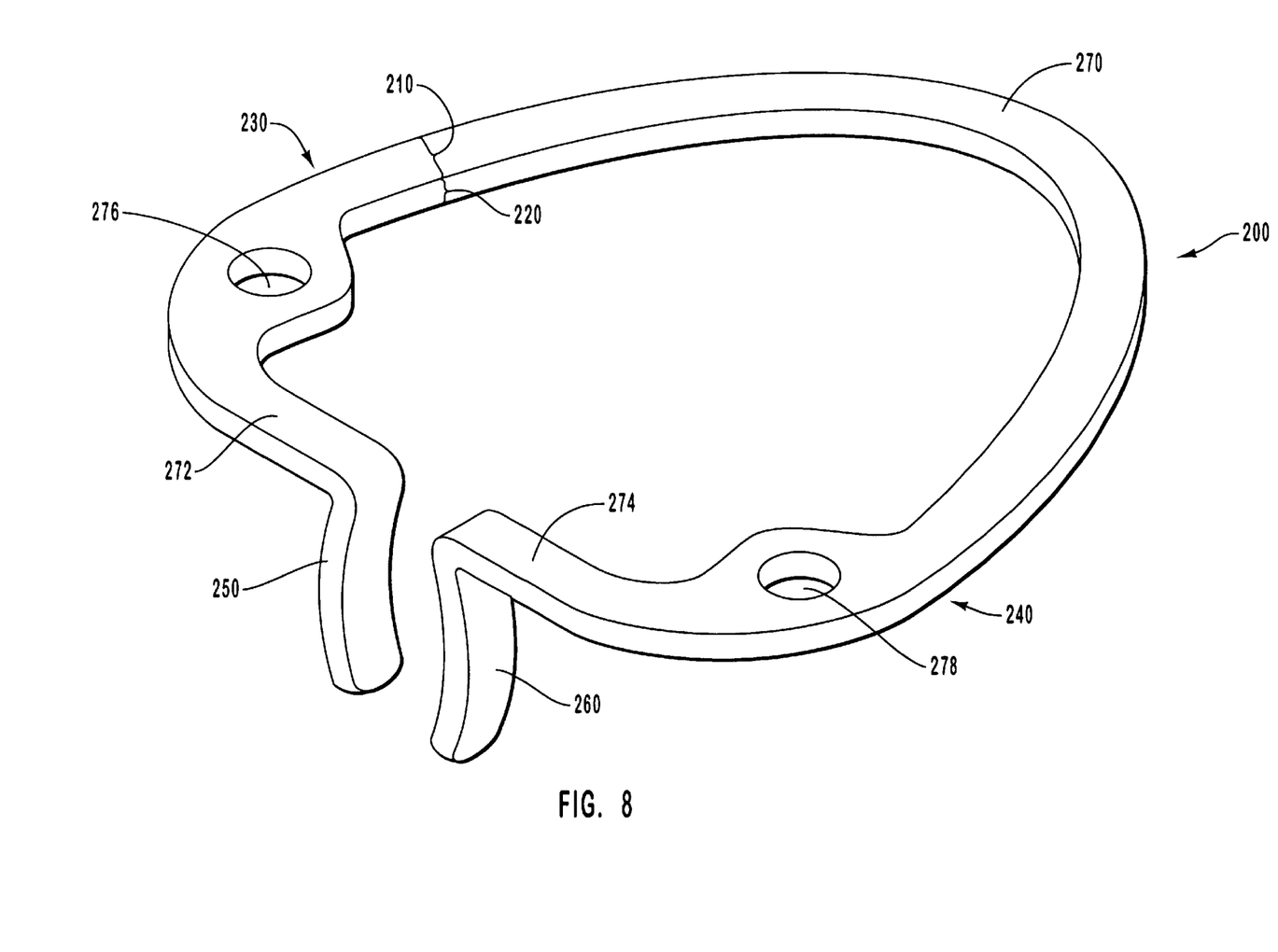
FIG. 8 is a perspective view of one embodiment of the matrix band retainer of the invention that includes a thin profile body member, tines, receptacle holes configured for securely receiving the prongs of a spreading device that can be used to separate the tines of the matrix band retainer, and crossbar members separating the tines from the receptacle holes.
Figure 9:
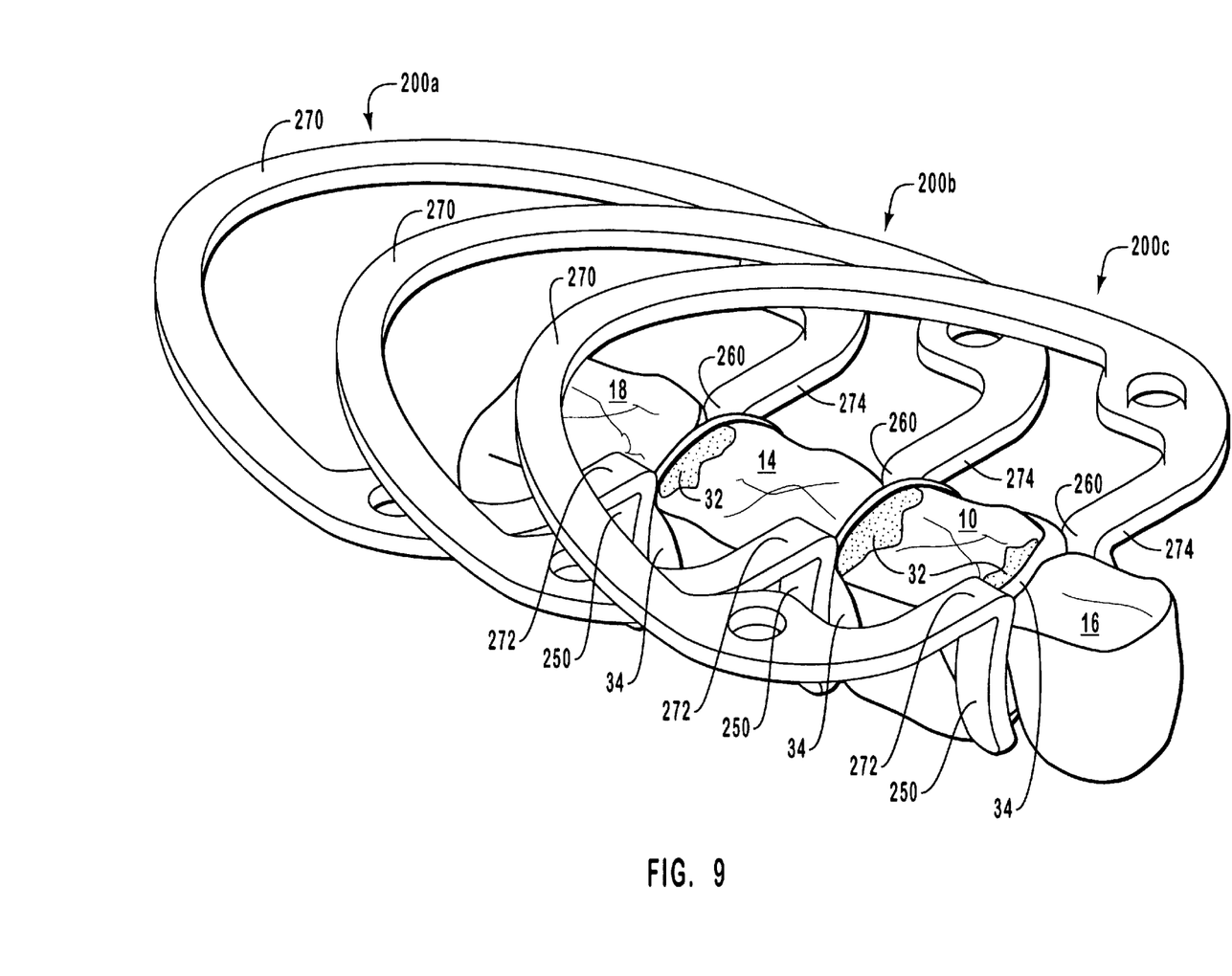
FIG. 9 is a perspective view of three of the matrix bands of FIG. 8 being used simultaneously to retain a pair of matrix bands placed within the interproximal spaces between two adjacent teeth.

According to yet another embodiment of the invention, as illustrated in FIGS. 8 and 9, a matrix band retainer 200 according to the invention generally comprises a thin profile. In other words, the body member 270 has a cross-sectional area, that arcuately extends from a first end 230 to a second end 240 of the body member 270 and that is defined by a width 210 that is substantially greater than the height or thickness 220 of the body member 270. As illustrated, the cross-sectional area of the body member 270 is rectangular, although other shapes can also be used such as oval or other rounded shapes. According to one embodiment, the thickness or height 220 of the body member 270 is about ¼ to about ½ the magnitude of the corresponding width 210. For instance, according to one preferred embodiment, the width 210 of the body member 270 is about 5 mm and the height 220 of the body member 270 is about 3 mm. The thin profile, as generally described below, is useful for facilitating the overlapping of the matrix band retainer 200. More particularly, the thin profile of the matrix band retainer 200 enables the matrix band retainer 200 to overlap at least a portion of another matrix band retainer 200 while reducing angular displacement of the tines 250 and 260, as shown and described more clearly in reference to FIG. 9.

As illustrated in FIG. 8, the tines 250 and 260 also have substantially rectangular cross-sectional areas. This is largely a function of manufacturing the matrix band retainer 200 out of a single rectangular piece of material. Accordingly, it will be appreciated that the tines can also comprise different shapes that are not rectangular. For instance, in one embodiment, not shown, the tines 250 and 260 may be defined by a substantially oval cross-sectional shape. An oval shape may be useful, for example, in minimizing any sharp edges that might abrade the dental surfaces during use.

One benefit of the embodiment shown in FIG. 8 is that the tines have a much larger surface area for making abutting contact with the matrix band compared to wedge-shaped tines. This allows the matrix band to more reliably hold and retain a matrix band in a desired wrapped-around configuration relative to the tooth.

Another characteristic of the present embodiment, as shown, is that the receptacle means, comprising hole formations 276 and 278, are located within the body member 270 adjacent the respective ends 230 and 240 of the body member 270. This embodiment is useful for further facilitating the ability of a rubber dam clamp spreading tool to spread the tines 250 and 260. In particular, the location of the hole formations 276 and 278 near the respective ends 276 and 278 of the body member 270 increases the leverage that can be applied at the hole formations 276 and 278 for flexing the body member 270 to separate the tines 250 and 260.

Another characteristic of this embodiment is that the hole formations 276 and 278 are spaced-apart from the tines 250 and 260 by a pair of crossbar members 272 and 274, respectively. This may be useful in reducing the likelihood that the prongs of the rubber dam clamp spreading tool will engage dental surfaces during placement and removal of the matrix band retainer 200. This may, in turn, reduce discomfort and agitation experienced by the patient. The crossbar members 272 and 274 are preferably co-planar to the body member 270.

In certain other embodiments (not shown) the hole formations 276 and 278, or any other receptacle means, may be disposed directly on the crossbar members 272 or 274, closer to the tines. In these other embodiments, it is preferred, but not required, that the receptacle means be disposed closer to the corresponding ends 230 and 240 of the body member 270 than to the tines 250 and 260, for reasons described above.

Turning now to FIG. 9, it is shown how the thin profile of the matrix band retainers of the invention can be beneficial when the matrix band retainers are applied in overlapping configurations. As shown, three matrix band retainers 200a, 200b, and 200c are positioned in an overlapping fashion for holding a plurality of matrix bands 34 against teeth 10 and 14. This configuration may be desired, for example, when filling a plurality of dental preparations 32 during a single session.

As shown, matrix band retainer 200b overlays matrix band retainer 200a, and matrix band retainer 200c overlays matrix band retainers 200a and 200b. It will be appreciated that the thin profile of the matrix band retainer 200a of the invention generally enables matrix band retainer 200b to overlay matrix band retainer 200a while still enabling the corresponding tines 250 and 260 of the matrix band retainer 200b to be held within a desired placement. Likewise, matrix band retainer 200c is able to maintain its tines 250 and 260 within a desired placement despite overlapping matrix band retainers 200a and 200b. It will further be appreciated by one skilled in the art that the thin profile of the present matrix band retainers provides an improvement over conventional matrix band retainers. In particular, conventional matrix band retainers do not have a thin profile, such that the body of existing matrix band retainers, by virtue of their thickness or height, cause overlaying matrix band retainers to be raised so high that the corresponding tines of the overlaying matrix band retainer can be excessively angularly displaced. This, in turn, may prevent them from holding a matrix band in an appropriate placement for providing form during the dental restoration procedure.

In contrast, the matrix band retainers of the present invention, when overlapping, will not cause significant angular displacement of the corresponding tines because the thin profile of the underlying body member reduces the angular displacement of the overlapping matrix band retainer. Although some displacement of the tines may be exhibited, it will be appreciated that the thin profile exhibited by the matrix band retainers of the present invention will greatly reduce the displacement that otherwise occurs with conventional matrix band retainers.

The invention, as it has been described herein, generally enables a matrix band retainer to be conformingly inserted into the interproximal spaces between adjacent teeth for holding a matrix band in a desired placement without independently causing separation of the teeth. The invention also enables the tines of the matrix band retainer to be spread apart by using a rubber dam clamp spreading tool in a secure and safe manner. The matrix band retainers of the invention also comprise thin profiles for facilitating overlapping uses. It will be appreciated that these benefits of the invention are advantages over the prior art.

It should also be appreciated that the present invention may be embodied in other forms without departing from its spirit or essential characteristics. As properly understood, the preceding description of specific embodiments is illustrative only and in no way restrictive. The scope of the invention is, therefore, indicated by the appended claims as follows.

What is claimed is:

1. A matrix band retainer comprising:
    a flexible body member which extends from a first end to a second end of the flexible body member, the flexible body member lying substantially in a plane and having a body thickness that is less than its body width in order for the body member of one matrix band to extend over the body member of another matrix band with reduced angular displacement when in use in a person's mouth compared to a body member in which the body thickness equals or exceeds its body width;
    first and second tines configured in shape and size to retain a matrix band within the interproximal spaces between a pair of adjacent teeth;
    first and second crossbar members interconnecting said first and second tines, respectively, with said first and second ends of said flexible body member; and
    receptacle means for receiving the prongs of a separating device that can be used to separate the tines of the matrix band retainer.

2. A matrix band retainer as recited in claim 1, wherein the matrix band retainer is configured to provide a holding force sufficient for retaining a matrix band within the interproximal spaces between a pair of adjacent teeth without separating the adjacent teeth.

3. A matrix band retainer as defined in claim 1, wherein the flexible body member has a substantially rectangular cross-sectional shape.

4. A matrix band retainer as defined in claim 1, wherein the body thickness is between about ¼ and about ½ of the body width.

5. A matrix band retainer as defined in claim 4, wherein the body width is about 5 mm and the body thickness is about 3 mm.

6. A matrix band retainer as defined in claim 1, wherein the matrix band retainer is configured such that, when the first and second tines are placed within interproximal spaces between two adjacent teeth, the body width has a substantial horizontal orientation relative to a patient's teeth and the body thickness has a substantially vertical orientation relative to the patient's teeth.

7. A matrix band retainer as defined in claim 1, wherein the first and second tines are disposed substantially perpendicular relative to the flexible body member.

8. A matrix band retainer as defined in claim 1, wherein the first and second tines are curved to approximately conform to the curvature of a patient's teeth.

9. A matrix band retainer as defined in claim 1, wherein the first and second tines have a substantially rectangular cross section.

10. A matrix band retainer as defined in claim 1, wherein the first and second tines have a substantially elliptical cross section.

11. A matrix band retainer as defined in claim 10, wherein the first and second crossbar members are substantially coplanar to the body member.

12. A matrix band retainer as defined in claim 1, wherein the receptacle means includes two hole formations, each hole formation configured to receive a prong of a tool that can be used to spread the first and second tines apart.

13. A matrix band retainer as recited in claim 12, wherein the hole formations are formed in the flexible body member.

14. A matrix band retainer as recited in claim 13, wherein each hole formation is disposed at a respective end of the body member.

15. A matrix band retainer as defined in claim 1, wherein the flexible body member comprises stainless spring steel.

16. A matrix band retainer as defined in claim 1, wherein the flexible body member is substantially arcuate.

17. A matrix band retainer as defined in claim 1, that, when used to retain a matrix band between two adjacent teeth, does not substantially separate the teeth.

18. A matrix band retainer comprising:

a flexible body member extending between a first end and a second end of the flexible body member, the flexible body member having a body width and a body thickness that is between about ¼ to about ½ of the body width in order for the body member of one matrix band to extend over the body member of another matrix band with reduced angular displacement when in use in a person's mouth compared to a body member in which the body thickness equals or exceeds its body width;

first and second tines configured in shape and size to retain a matrix band within interproximal spaces between the teeth;

first and second crossbar members interconnecting the first and second tines, respectively, with the first and second ends of the flexible body member; and receptacle means for receiving the prongs of a separating device that can be used to separate the tines of the matrix band retainer.

19. A matrix band retainer as recited in claim 18, wherein the body member and tines have a cross section that is elliptical or rectangular.

20. A matrix band retainer comprising:

a flexible body member having a substantially rectangular cross section and that arcuately extends between a first end and a second end of the flexible body member, the body member having a body width that is greater than its body thickness, with the thickness being at lest about ¼ of the body width, in order for the body member of one matrix band to extend over the body member of another matrix band with reduced angular displacement when in use in a person's mouth compared to a body member in which the body thickness equals or exceeds its body width;

first and second tines configured in shape and size to retain a matrix band within interproximal spaces between the teeth;

first and second crossbar members interconnecting the first and second tines, respectively, with the first and second ends of the flexible body member; and first and second hole formations within the body member configured to receive the prongs of a spreading device.

* * * * *

UNITED STATES PATENT AND TRADEMARK OFFICE
CERTIFICATE OF CORRECTION

PATENT NO.    : 6,589,053 B2
DATED         : July 8, 2003
INVENTOR(S)   : Dan J. Bills It is certified that error appears in the above-identified patent and that said Letters Patent is hereby corrected as shown below:

Column 7,
Line 51, after "and" insert -- 60 --

Signed and Sealed this

Twenty-first Day of September, 2004

JON W. DUDAS
*Director of the United States Patent and Trademark Office*